United States Patent
Page et al.

(10) Patent No.: US 11,253,464 B2
(45) Date of Patent: *Feb. 22, 2022

(54) ANHYDROUS COMPOSITION INCLUDING A LIPOPHILIC GELLING AGENT, AT LEAST TWO DIFFERENT FILLERS AND AN OIL PHASE

(71) Applicant: L'OREAL, Paris (FR)

(72) Inventors: Valerie Page, Saou (FR); Sophie Guilbaud, Cliousclat (FR); Celine Demarcq, Piegros la Clastre (FR)

(73) Assignee: L'OREAL, Paris (FR)

( * ) Notice: Subject to any disclaimer, the term of this patent is extended or adjusted under 35 U.S.C. 154(b) by 266 days.

This patent is subject to a terminal disclaimer.

(21) Appl. No.: 15/322,675

(22) PCT Filed: Jun. 30, 2015

(86) PCT No.: PCT/FR2015/051800
§ 371 (c)(1),
(2) Date: Dec. 28, 2016

(87) PCT Pub. No.: WO2016/001578
PCT Pub. Date: Jan. 7, 2016

(65) Prior Publication Data
US 2017/0172904 A1    Jun. 22, 2017

(30) Foreign Application Priority Data
Jun. 30, 2014 (FR) ...................... 1456139

(51) Int. Cl.
| | |
|---|---|
| *A61K 8/92* | (2006.01) |
| *A61K 8/25* | (2006.01) |
| *A61K 8/44* | (2006.01) |
| *A61K 8/73* | (2006.01) |
| *A61Q 1/00* | (2006.01) |
| *A61K 8/37* | (2006.01) |
| *A61K 8/02* | (2006.01) |
| *A61K 8/04* | (2006.01) |
| *A61Q 19/00* | (2006.01) |

(52) U.S. Cl.
CPC ............. *A61K 8/922* (2013.01); *A61K 8/025* (2013.01); *A61K 8/04* (2013.01); *A61K 8/25* (2013.01); *A61K 8/375* (2013.01); *A61K 8/44* (2013.01); *A61K 8/73* (2013.01); *A61K 8/731* (2013.01); *A61K 8/732* (2013.01); *A61Q 1/00* (2013.01); *A61Q 19/00* (2013.01); *A61K 2800/31* (2013.01)

(58) Field of Classification Search
None
See application file for complete search history.

(56) References Cited

U.S. PATENT DOCUMENTS

| | | | | |
|---|---|---|---|---|
| 5,024,831 | A * | 6/1991 | Kurisaki | A61K 8/731 424/489 |
| 2004/0096472 | A1* | 5/2004 | Tournilhac | A61K 8/31 424/401 |
| 2006/0034788 | A1* | 2/2006 | Horino | A61K 8/25 424/63 |
| 2010/0183536 | A1* | 7/2010 | Ansmann | A61K 8/31 424/65 |
| 2017/0143616 | A1* | 5/2017 | Page | A61K 8/25 |

FOREIGN PATENT DOCUMENTS

| | | | |
|---|---|---|---|
| FR | 2 843 018 | A1 | 2/2004 |
| FR | 2 975 297 | A1 | 11/2012 |

OTHER PUBLICATIONS

International Search Report dated Sep. 7, 2015, in PCT/FR2015/051800 filed Jun. 30, 2015.

* cited by examiner

*Primary Examiner* — Aradhana Sasan
(74) *Attorney, Agent, or Firm* — Oblon, McClelland, Maier & Neustadt, L.L.P.

(57) ABSTRACT

Anhydrous compositions including from 3% to 15% by weight of at least one lipophilic gelling agent, from 10% to 50% by weight of fillers including at least 5% by weight of a first filler and at least 5% by weight of a second filler different from the first; and from 40% to 85% by weight of at least one fatty phase are provided.

30 Claims, No Drawings

ANHYDROUS COMPOSITION INCLUDING A LIPOPHILIC GELLING AGENT, AT LEAST TWO DIFFERENT FILLERS AND AN OIL PHASE

The present invention relates to an anhydrous composition comprising from 3% to 15% by weight of at least one lipophilic gelling agent, from 10% to 50% by weight of fillers including at least 5% by weight of a first filler and at least 5% by weight of a second filler different from the first, and from 40% to 85% by weight of at least one fatty phase. The invention relates in particular to the cosmetic field, and especially to the field of caring for and/or making up keratin materials, especially the skin, the lips, the hair or the nails, preferably the skin.

In the field of cosmetic compositions for caring for and/or making up the skin, it is known practice to use mineral or organic fillers with a soft-focus effect which absorb fat, give an astounding "photoshop" optical effect, and also a very soft feel, for making the skin matt, and/or for optically smoothing the microrelief, filling wrinkles, hiding skin imperfections and better reflecting light.

However, the use of these fillers is generally accompanied by a dry, rough feel, fluffing, white marks and a lack of comfort that are unacceptable to the user.

In order to overcome this problem and to afford comfortable care that has a soft-focus effect, oily presentation forms are currently proposed on the cosmetic market. However, these forms have the drawbacks associated with the presence of large contents of fatty phase in the composition, namely producing shiny skin and/or the sensation of greasy and/or tacky skin.

It is also known practice to use crosslinked silicones to satisfy this problem. The reason for this is that raw materials of this type allow a matt effect and a soft-focus effect to be combined, but have the drawback of being characterized by a relatively unpleasant hot, greasy feel, with a "mask" effect.

Thus, it is difficult to reconcile in the same composition opposing technical performance qualities, for instance a matt result (which may make the skin dry) and moisturization (which may make the skin shiny).

It thus remains difficult for a person skilled in the art to propose homogeneous compositions that are capable of affording an immediate visual result on the skin with a sensation of lightness and comfort on application, this expected immediate result preferentially being good covering of color imperfections and/or relief imperfections.

There thus remains a need for preparing cosmetic compositions which can solve the technical problem of making the skin's microrelief matt and/or optically smooth, filling wrinkles, hiding skin imperfections and better reflecting light, while at the same time affording a pleasant feel especially when applied, and a very soft skin finish with no "mask" effect, and which allow the skin to breathe.

The Applicant has discovered that this need can be satisfied by combining, in an anhydrous composition comprising a fatty phase, a lipophilic gelling agent and at least two suitably selected different fillers, in appropriate amounts.

This combination makes it possible to satisfy the problem mentioned above by proposing an oily presentation form endowed with a novel sensory effect both on application and on the skin finish, without neglecting the cosmetic qualities.

More specifically, one subject of the present invention is an anhydrous composition comprising:
  from 3% to 15% by weight of at least one lipophilic gelling agent;
  from 10% to 50% by weight of fillers including at least 5% by weight of a first filler and at least 5% by weight of a second filler different from the first; and
  from 40% to 85% by weight of at least one fatty phase;
  the weight amounts being given relative to the total weight of the composition.

The present invention makes it possible to obtain a novel presentation form that is most particularly advantageous with regard to its technical performance qualities and the sensory results it affords the user when it is applied to keratin materials, and in particular to the skin. Thus, the composition in accordance with the invention affords comfortable anhydrous care with a soft-focus effect, i.e. it can render the skin microrelief matt and/or optically smooth, fill wrinkles, hide skin imperfections and better reflect light, while at the same time giving a pleasant feel and a novel sensory effect, that of oily care that is not greasy or tacky, with powdery transformation especially when it is applied, and with a velvety skin finish, and which allows the skin to breathe.

The composition satisfies the consumers' need for an oily product without having the application and skin finish drawbacks thereof generated by a conventional type of oily presentation form.

The comfort on application is reflected especially by an absence of tautness, of dryness sensations and/or of tacky and/or greasy sensations.

The composition according to the invention is stable, especially over time and/or with respect to temperature variations, while at the same time having good cosmetic and sensory properties.

The term "stable" means stable at room temperature (25° C.) for at least 1 month, preferably for at least 2 months.

The composition affords all the benefits of an oil without having the greasy feel or the shiny appearance thereof. The skin finish is homogeneous and comfortable. The composition is friendly to the skin, it is pleasant and does not leave the skin greasy or tacky. The texture is soft and pleasant, and the composition is easy to take up. It affords an optical and tactile effect for immediately correcting the surface appearance of the skin, by attenuating the shadow areas of the skin relief such as wrinkles, fine lines, dilated pores and other skin imperfections. It fades out the signs of fatigue. It smooths and refines the skin grain, restoring the skin's radiance and freshness, for a natural result.

A subject of the present invention is also a cosmetic process for making up and/or caring for keratin materials, comprising a step of applying a composition as defined above to said keratin materials.

As the composition of the invention is intended for topical application to the skin or the integuments, it comprises a physiologically acceptable medium, i.e. a medium that is compatible with all keratin materials, such as the skin, the nails, mucous membranes and keratin fibers (such as the hair or the eyelashes).

For the purposes of the present invention, the term "anhydrous" refers to a composition comprising a content of less than or equal to 1% by weight and preferably less than or equal to 0.5% by weight of water relative to the total weight of said composition, or is even free of water. Where appropriate, such small amounts of water may especially be introduced by ingredients of the composition that may contain residual amounts thereof.

In the text hereinbelow, the expression "at least one" is equivalent to "one or more" and, unless otherwise indicated, the limits of a range of values are included in that range.

Lipophilic Gelling Agents

For the purposes of the present invention, the term "lipophilic gelling agent" means a compound that is capable of gelling the fatty phase of the composition according to the invention.

The lipophilic gelling agent(s) are liposoluble or lipodispersible.

According to a particular embodiment of the invention, the lipophilic gelling agent(s) are organic or mineral.

According to another particular embodiment of the invention, the lipophilic gelling agent(s) are non-silicone-based.

The gelling agent(s) that may be used in the context of the invention may be organic, polymeric or molecular lipophilic gelling agents.

As examples of lipophilic gelling agents that may be used in the context of the invention, mention may be made of modified natural micas such as aluminum magnesium potassium fluorosilicate, in particular the product sold by the company Sensient under the name Submica M, fatty acid esters of dextrin, such as dextrin palmitate, in particular the product sold by the company Chiba Flour Milling under the name Rheopearl TL2-OR, or the dextrin palmitate sold by the same company under the name Rheopearl KL2-OR, and also dextrin myristate, in particular the product sold by the company Chiba Flour Milling under the name Rheopearl MKL2, triesters of a C8-C30 fatty acid and of mono- or polyglycerol, such as glyceryl trihydroxystearate, in particular the product sold by the company Elementis under the name Thixcin R or Rheocin sold by the company Byk Additives & Instruments.

According to a particular embodiment of the invention, the lipophilic gelling agent(s) are organic.

According to a particular embodiment, the lipophilic gelling agent(s) that may be used in the context of the invention are chosen from fatty acid esters of dextrin and triesters of a C8-C30 fatty acid and of mono- or polyglycerol.

Fatty Acid Esters of Dextrin

The fatty acid esters of dextrin used according to the invention may be chosen especially from monoesters or polyesters of dextrin and of at least one fatty acid, corresponding to formula (C):

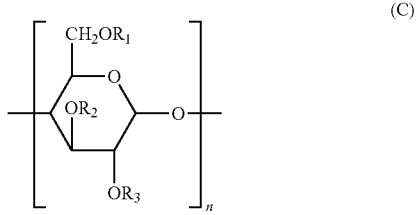

(C)

in which:

n is an integer ranging from 3 to 150, especially from 10 to 100 and preferably from 15 to 40; the radicals $R_1$, $R_2$ and $R_3$ represent a hydrogen atom or an acyl group (R—CO—) in which the radical R is a linear or branched, saturated or unsaturated hydrocarbon-based group containing from 6 to 50, especially from 8 to 30, or even 12 to 22 and better still 12 to 18 carbon atoms, with the proviso that at least one of said radicals $R_1$, $R_2$ or $R_3$ is other than a hydrogen atom.

In particular, $R_1$, $R_2$ and $R_3$ may represent hydrogen or an acyl group (R—CO—) in which R is a hydrocarbon-based radical as defined previously, with the proviso that at least two of said radicals $R_1$, $R_2$ or $R_3$ are identical and other than hydrogen.

The radicals $R_1$, $R_2$ and $R_3$ may all represent an acyl group (R—CO), which is identical or different and especially identical.

The radical R—CO— of the dextrin ester of formula (C) may be chosen especially from caprylyl, caproyl, lauroyl, myristyl, palmityl, stearyl, eicosanyl, docosanoyl, isovaleryl, 2-ethylbutyryl, ethylmethylacetyl, isoheptanyl, 2-ethylhexanyl, isononanyl, isodecanyl, isotridecanyl, isomyristyl, isopalmityl, isostearyl, isohexanyl, decenyl, dodecenyl, tetradecenyl, myristyl, hexadecenoyl, palmitoleyl, oleyl, elaidyl, eicosenyl, sorbyl, linoleyl, linolenyl, punicyl, arachidonyl and stearolyl radicals, and mixtures thereof.

The radical R—CO is advantageously linear. R—CO is preferably a palmityl radical or a myristyl radical, and even more preferentially a palmityl radical.

n advantageously ranges from 25 to 35, preferably from 27 to 33, and better still is equal to 30.

Preferably, at least one dextrin palmitate and/or at least one dextrin myristate is used as fatty acid ester of dextrin. They may be used alone or as a mixture with other esters.

Advantageously, the fatty acid ester of dextrin has a degree of substitution of less than or equal to 2.5, especially ranging from 1.5 to 2.5, on the basis of one glucose unit. The weight-average molecular weight of the dextrin ester may in particular be from 10 000 to 150 000, especially from 12 000 to 100 000 and even from 15 000 to 80 000.

Dextrin esters are commercially available, in particular dextrin palmitates, for example under the name Rheopearl TL2-OR or Rheopearl KL2-OR from the company Chiba Flour Milling, and under the name Rheopearl KS from the company Chiba Flour Milling, and dextrin myristates, for example under the name Rheopearl MKL2 from the company Chiba Flour Milling.

According to a particular embodiment of the invention, use will be made of a mixture of a fatty acid ester of dextrin whose degree of substitution is less than 2 on the basis of one glucose unit and of a fatty acid ester of dextrin whose degree of substitution is greater than 2 on the basis of one glucose unit, as described in patent application FR 2 843 020.

According to one embodiment, the fatty acid ester of dextrin whose degree of substitution is less than 2 on the basis of one glucose unit advantageously corresponds to formula (IV) below:

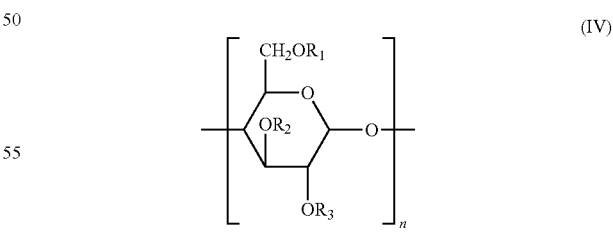

(IV)

in which:

the radicals $R_1$, $R_2$ and $R_3$ represent a hydrogen atom or an acyl group (R—CO—) in which the radical R is a linear or branched, saturated or unsaturated hydrocarbon-based group containing from 6 to 50, especially from 8 to 30, or even 12 to 22 and better still 12 to 18 carbon atoms, with the proviso that at least one of said radicals $R_1$, $R_2$ or $R_3$ is other than a hydrogen atom;

n is an integer ranging from 3 to 150, especially from 10 to 100 and preferably from 15 to 40.

The radical R—CO— of the dextrin ester of formula (IV) may be chosen especially from caprylyl, caproyl, lauroyl, myristyl, palmityl, stearyl, eicosanyl, docosanoyl, isovaleryl, 2-ethylbutyryl, ethylmethylacetyl, isoheptanyl, 2-ethylhexanyl, isononanyl, isodecanyl, isotridecanyl, isomyristyl, isopalmityl, isostearyl, isohexanyl, decenyl, dodecenyl, tetradecenyl, myristyl, hexadecenoyl, palmitoleyl, oleyl, elaidyl, eicosenyl, sorbyl, linoleyl, linolenyl, punicyl, arachidonyl and stearolyl radicals, and mixtures thereof.

The radical R—CO is advantageously linear. The radical R—CO is preferably a palmityl radical or a myristyl radical, and even more preferentially a palmityl radical.

n advantageously ranges from 25 to 35, preferably from 27 to 33, and better still is equal to 30.

Preferably, use is made of a fatty acid ester of dextrin whose degree of substitution is less than 2 on the basis of one glucose unit, such that the degree of substitution is less than 1.9, preferably less than 1.8 and more preferably is between 1.5 and 1.7. Some of these dextrin esters are commercially available, especially under the name Rheopearl TL from the company Chiba Flour Milling.

The weight-average molecular weight of the fatty acid ester of dextrin whose degree of substitution is less than 2 on the basis of one glucose unit is preferably between 10 000 and 30 000, more preferably between 15 000 and 20 000. The weight-average molecular weight is determined by gas chromatography, with polystyrene calibration.

According to one embodiment, the fatty acid ester of dextrin whose degree of substitution is greater than 2 on the basis of one glucose unit corresponds to formula (V):

$$\left[\begin{array}{c} CH_2OR'_1 \\ \diagup O \diagdown \\ \diagup \diagdown \\ R'_2O \quad OR'_3 \end{array}\right]_n \quad (V)$$

in which:

the radicals $R'_1$, $R'_2$ and $R'_3$, which may be identical or different, are chosen from a hydrogen atom or an acyl group (R'—CO—) in which the radical R' is a linear or branched, saturated or unsaturated hydrocarbon-based group containing from 6 to 50, especially from 8 to 30, or even 12 to 22 and better still 12 to 18 carbon atoms, with the proviso that at least one of said radicals $R'_1$, $R'_2$ or $R'_3$ is other than a hydrogen atom;

n is an integer ranging from 3 to 150, especially from 10 to 100 and preferably from 15 to 40. R' and n may have the same meaning as R and n described previously.

Advantageously, the radicals $R'_1$, $R'_2$ and $R'_3$ are identical, with the proviso that at least one of said radicals $R'_1$, $R'_2$ or $R'_3$ is other than a hydrogen atom.

Preferably, use is made of a fatty acid ester of dextrin whose degree of substitution is greater than 2 on the basis of one glucose unit, such that the degree of substitution is greater than 2.1, preferably between 2.1 and 2.3.

The weight-average molecular weight of the fatty acid ester of dextrin whose degree of substitution is greater than 2 on the basis of one glucose unit is preferably between 10 000 and 30 000, more preferably between 15 000 and 20 000. The weight-average molecular weight is determined by gas chromatography, with polystyrene calibration.

As examples of dextrin esters of formula (V) according to the invention, mention may be made of Rheopearl KL sold by the company Chiba Flour Milling.

Triesters of Fatty Acid and of mono- or polyglycerol

According to a particular embodiment, the triester(s) of fatty acid and of mono- or polyglycerol are triesters of fatty acid and of monoglycerol.

The term "fatty acid" means a linear or branched, saturated or unsaturated acid, comprising from 8 to 30 carbon atoms, preferably from 10 to 24 carbon atoms, even more preferentially from 12 to 22 and better still from 16 to 20 carbon atoms, optionally substituted with one or more hydroxyl groups. According to a particular embodiment of the invention, the fatty acid(s) are linear and saturated, substituted with at least one hydroxyl group.

The fatty acids may be chosen from oleic acid, lauric acid, palmitic acid, myristic acid, stearic acid, linoleic acid, capric acid and behenic acid, optionally substituted with at least one hydroxyl group, or mixtures thereof. Preferably, the fatty acid(s) are chosen from stearic acid, stearic acids substituted with at least one hydroxyl group, and mixtures thereof, and are more preferentially chosen from stearic acid, 12-hydroxystearic acid, and mixtures thereof, and even better still it is 12-hydroxystearic acid.

According to a particular embodiment of the invention, the triester of a C8-C30 fatty acid and of mono- or polyglyceryl is glyceryl tris(12-hydroxystearate).

As examples of triester of a C8-C30 fatty acid and of mono- or polyglycerol, mention may be made of glyceryl tri(hydroxystearate) (INCI name: Trihydroxystearin), for instance the product sold by the company Elementis under the name Thixcin R or the product sold by the company Byk Additives & Instruments under the name Rheocin.

According to a particular embodiment of the invention, the lipophilic gelling agent(s) that may be used in the context of the invention are chosen from fatty acid esters of dextrin, preferably dextrin palmitate and dextrin myristate.

According to another particular embodiment of the invention, the lipophilic gelling agent(s) that may be used in the context of the invention are chosen from triesters of a C8-C30 fatty acid and of monoglycerol, preferably glyceryl tri(hydroxystearate), and even more preferentially glyceryl tris(12-hydroxystearate).

The lipophilic gelling agent(s) are present in the composition in accordance with the invention in an amount of between 3% and 15% by weight, preferably from 5% to 12% by weight and even more preferentially from 8.5% to 10% by weight, relative to the total weight of the composition.

Fillers

The composition in accordance with the invention comprises from 10% to 50% by weight of fillers, relative to the total weight of the composition, including at least 5% by weight of a first filler and at least 5% by weight of a second filler different from the first, the first filler and the second filler preferably being chosen from spherical cellulose particles, powders of an N-acylamino acid bearing a C8-C22 acyl group, polyamide particles and spherical porous silica particles.

The term "filler" should be understood as meaning colorless or white, mineral or synthetic particles of any shape, which are insoluble in the medium of the composition, irrespective of the temperature at which the composition is manufactured.

The filler(s) may especially be organic fillers and/or mineral fillers.

The fillers used in the present invention may be characterized by their specific surface area per unit mass or per unit volume, their size expressed as the volume-mean diameter D(4,3), their non-tapped density and/or their oil-absorbing capacity.

The sizes of the fillers may be measured by static light scattering using a commercial particle size analyzer such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is in particular described in the publication by Van de Hulst, H. C., Light Scattering by Small Particles, Chapters 9 and 10, Wiley, N.Y., 1957.

The specific surface area per unit mass may be determined by the nitrogen absorption method, known as the BET (Brunauer-Emmett-Teller) method, described in The Journal of the American Chemical Society, vol. 60, page 309, February 1938 and corresponding to international standard ISO 5794/1 (annex D). The BET specific surface area corresponds to the total specific surface area of the particles under consideration.

The specific surface area per unit volume is given by the relationship: $S_V = S_M \times \rho$, where $\rho$ is the tapped density, expressed in g/cm3, and $S_M$ is the specific surface area per unit mass, expressed in $m^2/g$, as defined above.

In the context of the present invention, this density, known as the tapped density, may be assessed according to the following protocol: 40 g of powder are poured into a graduated measuring cylinder; the measuring cylinder is then placed on the Stav 2003 device from Stampf Volumeter; the measuring cylinder is subsequently subjected to a series of 2500 tapping actions (this operation is repeated until the difference in volume between two consecutive tests is less than 2%) and then the final volume Vf of tapped powder is measured directly on the measuring cylinder. The tapped density is determined by the ratio m/Vf, in this instance 40/Vf (Vf being expressed in $cm^3$ and m in g).

The oil-absorbing capacity, measured at the wet point and denoted Wp, corresponds to the amount of oil which it is necessary to add to 100 g of particles in order to obtain a homogeneous paste.

It is measured according to the "wet point" method or the method for determining the oil uptake of a powder described in standard NF T 30-022. It corresponds to the amount of oil adsorbed onto the available surface of the powder and/or absorbed by the powder by measurement of the wet point, described below:

An amount m=2 g of powder is placed on a glass plate and then the oil (isononyl isononanoate) is added dropwise. After addition of 4 to 5 drops of oil to the powder, mixing is performed using a spatula, and addition of oil is continued until conglomerates of oil and powder have formed. From this point, the oil is added at the rate of one drop at a time and the mixture is subsequently triturated with the spatula. The addition of oil is stopped when a firm, smooth paste is obtained. This paste must be able to be spread over the glass plate without cracks or the formation of lumps. The volume Vs (expressed in ml) of oil used is then noted.

The oil uptake corresponds to the ratio Vs/m.

According to a particular embodiment, the fillers used in the present invention have an oil-absorbing capacity of from 0.25 to 3.5 mL/g, preferably from 0.93 to 2.5 mL/g, or even from 1.25 to 2.5 mL/g.

According to a particular embodiment, the fillers used in the present invention have a size, expressed as the volume-mean diameter D(4,3), ranging from 0.1 µm to 40 µm, preferably from 0.5 µm to 20 µm and even more preferentially from 1 µm to 16 µm.

According to a particular embodiment of the invention, the fillers used in the present invention have a heterogeneous particle size, i.e. a large particle size distribution for a given size expressed as the volume-mean diameter.

According to a particular embodiment, the fillers used in the present invention have a non-tapped density ranging from 0.2 $g/cm^3$ to 2.2 $g/cm^3$.

Organic Fillers

In the present patent application, the term "organic filler" means any organic solid that is insoluble in the medium at room temperature (25° C.).

The term "organic" refers to any compound or polymer whose chemical structure comprises at least one or more carbon atoms.

As organic fillers that may be used in the composition of the invention, examples that may be mentioned include polyamide (Nylon®) particles and especially those sold under the name Orgasol® by the company Atochem; polyethylene powders; microspheres based on acrylic copolymers, such as those made of ethylene glycol dimethacrylate/lauryl methacrylate copolymer sold by the company Dow Corning under the name Polytrap®; polymethyl methacrylate microspheres, sold under the name Microsphere M-100® by the company Matsumoto or under the name Covabead LH85® by the company Wackherr; ethylene-acrylate copolymer powders, such as those sold under the name Flobeads® by the company Sumitomo Seika Chemicals; expanded powders such as hollow microspheres and especially microspheres formed from a terpolymer of vinylidene chloride, acrylonitrile and methacrylate and sold under the name Expancel® by the company Kemanord Plast under the references 551 DE 12® (particle size of about 12 µm), 551 DE 20® (particle size of about 30 µm), 551 DE 50® (particle size of about 40 µm), or the microspheres sold under the name Micropearl F 80 ED® by the company Matsumoto; powders of natural organic materials such as polysaccharide powders, and in particular starch powders, especially of crosslinked or non-crosslinked corn, wheat or rice starch, powders of starch crosslinked with octenylsuccinic anhydride, sold under the name Dry-Flo® by the company National Starch, powders of waxy corn starch, such as those sold under the names C* Gel 04201 by the company Cargill, Amidon de Maïs B by the company Roquette, and Organic Corn Starch by the company Draco Natural Products; cellulose particles such as those sold under the name Cellulobeads by the company Daito Kasei Kogyo; mention may also be made of the Tencel range from the company Lenzing; silicone resin microbeads such as those sold under the name Tospearl by the company Toshiba Silicone, especially Tospearl 240; amino acid powders such as the lauroyllysine powder sold under the name Amihope LL-11® by the company Ajinomoto; particles of wax microdispersion, which preferably have mean sizes of less than 25 µm and especially ranging from 0.5 µm to 25 µm, and which are formed essentially from a wax or a mixture of waxes, such as the products sold under the name Aquacer by the company Byk Cera, and especially: Aquacer 520 (mixture of synthetic and natural waxes), Aquacer 514® or 513® (polyethylene wax), Aquacer 511® (polymeric wax), or such as the products sold under the name Jonwax 120 by the company Johnson Polymer (mixture of polyethylene wax and paraffin wax) and under the name Ceraflour 961® by the company Byk Cera (micronized modified polyethylene wax); and mixtures thereof.

According to a particular embodiment of the invention, the organic filler(s) are chosen from spherical cellulose particles, powders of an N-acylamino acid bearing a C8-C22 acyl group, and polyamide particles, and mixtures thereof, and are preferably chosen from spherical cellulose particles and powders of an N-acylamino acid bearing a C8-C22 acyl group, and mixtures thereof.

In the context of the present invention, the term "spherical particles" means particles in the form or substantially in the form of a sphere, which are insoluble in the medium of the composition according to the invention, even at the melting point of the medium (about 100° C.).

According to a particular embodiment, the spherical cellulose particles that may be used in the context of the invention are microparticles. Preferably, they have a size, expressed as the volume-mean particle diameter D(4,3), ranging from 0.1 to 35 μm, preferably from 1 to 20 μm and more particularly from 4 to 15 μm.

Examples of spherical cellulose microparticles that may especially be mentioned include the solid cellulose beads sold under the names Cellulobeads D-10, Cellulobeads D-5 and Cellulobeads USF by the company Daito Kasei Kogyo.

The N-acylamino acids comprise an acyl group containing from 8 to 22 carbon atoms, for instance a 2-ethylhexanoyl, caproyl, lauroyl, myristoyl, palmitoyl, stearoyl or cocoyl group. The amino acid may be, for example, lysine, glutamic acid or alanine, preferably lysine.

According to a particular embodiment, the N-acylamino acid(s) comprise an acyl group containing from 10 to 14 carbon atoms. Preferably, it is a lauroyl group. Advantageously, the N-acylamino acid powder may be a lauroyllysine powder such as the product sold under the name Amihope LL by the company Ajinomoto or the product sold under the name Corum 5105 S by the company Corum.

Mineral Fillers

In the present patent application, the term "mineral filler" means any mineral solid that is insoluble in the medium at room temperature (25° C.).

The term "mineral" refers to any compound or polymer whose chemical structure does not comprise any carbon atoms.

As an example of mineral fillers, mention may be made of spherical porous silica particles with a particle size expressed as the volume-mean particle diameter D(4,3) ranging from 0.5 μm to 30 μm, more particularly from 1 μm to 20 μm and preferentially from 1 μm to 16 μm.

In the present patent application, the term "spherical particles" means particles in the form or substantially in the form of a sphere, which are insoluble in the medium of the composition according to the invention, even at the melting point of the medium (about 100° C.).

According to a particular embodiment, they have a specific surface area ranging from 30 m$^2$/g to 1000 m$^2$/g and more particularly from 150 m$^2$/g to 800 m$^2$/g.

According to another particular embodiment, they have an oil-absorbing capacity ranging from 0.15 to 5 ml/g and more particularly from 1.30 to 1.90 ml/g.

As examples of porous silica microbeads, use may be made of the following commercial products: Silica Beads SB-150, SB-300 or SB 700, preferentially SB 300 from the company Miyoshi Kasei; the Sunsphere range from the company Asahi Glass AGC SI-TECH, especially Sunsphere H-51 or Sunsphere 12L, Sunsphere H-201, H-52 and H-53; Sunsil 130 from the company Sunjin; Spherica P-1500 from the company Ikeda Corporation; Sylosphere from the company Fuji Silysia; the Silica Pearl and Satinier ranges from the company JGC Catalysts and Chemicals, more particularly Satinier M13 and M16, the silicas MSS-500 from the company Kobo, and more particularly MSS-500-20N, and also Silica Shells from the company Kobo.

Mention may also be made of zeolites, such as the products sold by the company Zeochem under the names Zeoflair 300, Zeoflair 200, Zeoflair 100, X-Mol and X-Mol MT.

A zeolite, or zeolite, is a crystal formed from an aluminosilicate microporous backbone, the connected empty spaces of which are initially occupied by cations and water molecules. They are also referred to as molecular sieves.

Mention may also be made of calcium magnesium carbonate, such as the products sold by the company Imerys under the name Calcidol, by the company LCW (Sensient) under the name Carbomat or by the company Omya under the name Omyacare S 60-AV.

Mention may also be made of lamellar mineral particles, such as talcs, micas or nacres, and mixtures thereof.

Talcs are hydrated magnesium silicates usually comprising aluminum silicate. The crystal structure of talc consists of repeated layers of a sandwich of brucite between layers of silica.

More particularly, the lamellar particles are chosen from talcs.

Advantageously, use is more particularly made, in the composition of the invention, as lamellar particles, of talc, such as the products sold under the names Luzenac Pharma M and UM by the company Imerys, Rose Talc and Talc SG-2000 by the company Nippon Talc; mica, such as the products sold under the names Mica M RP and Silk Mica by the company Merck; titanium micas such as mica/titanium oxide/brown iron oxide (CTFA: Mica/Iron oxides/Titanium dioxide), sold under the name Cloisonne Rouge Flambe 440 X by the company Engelhard. A mica that may be mentioned is the mica sold under the name Sericite S-152-BC by the company Miyoshi Kasei.

Among the mineral fillers, mention may be made of perlite particles and preferably expanded perlite particles.

The perlites that may be used according to the invention are generally aluminosilicates of volcanic origin and have the composition:

70.0-75.0% by weight of silica $SiO_2$;
12.0-15.0% by weight of oxide of aluminum oxide $Al_2O_3$;
3.0-5.0% of sodium oxide $Na_2O$;
3.0-5.0% of potassium oxide $K_2O$;
0.5-2% of iron oxide $Fe_2O_3$;
0.2-0.7% of magnesium oxide MgO;
0.5-1.5% of calcium oxide CaO;
0.05-0.15% of titanium oxide $TiO_2$.

Mention may be made especially of the perlites sold under the names Optimat 2550 OR by the company World Minerals, and Europerl EMP-2 and Europerl 1 by the company Imerys.

According to a particular embodiment, the mineral filler(s) that may be used in the context of the invention are chosen from spherical porous silica particles, and preferably spherical porous silica microparticles.

According to a first embodiment of the invention, the composition comprises at least two different fillers chosen from organic fillers. Preferably, the composition comprises at least two different fillers, one of which is chosen from spherical cellulose particles and the other is chosen from powders of an N-acylamino acid bearing a C8-C22 acyl group.

According to a second embodiment of the invention, the composition comprises at least two different fillers, one of which is chosen from organic fillers and the other is chosen from mineral fillers. Preferably, the composition comprises at least two different fillers, one of which is chosen from spherical cellulose particles, powders of an N-acylamino acid bearing a C8-C22 acyl group and polyamide particles, preferably spherical cellulose particles and powders of an N-acylamino acid bearing a C8-C22 acyl group, and the other is chosen from spherical porous silica particles, in particular spherical porous silica microparticles.

According to a particular embodiment, the composition comprises at least two different fillers, one of which is chosen from spherical cellulose particles and the other is chosen from spherical porous silica particles, in particular spherical porous silica microparticles.

According to another particular embodiment, the composition comprises at least two different fillers, one of which is chosen from powders of an N-acylamino acid bearing a C8-C22 acyl group and the other is chosen from spherical porous silica particles, in particular spherical porous silica microparticles.

According to a specific embodiment, the composition in accordance with the invention comprises at least two different fillers chosen from spherical porous silica particles, preferably spherical porous silica microparticles, spherical cellulose particles and powders of an N-acylamino acid bearing a C8-C22 acyl group.

According to a third embodiment of the invention, the composition comprises at least three fillers that are different from each other, one of which is chosen from mineral fillers and the other two are chosen from organic fillers. Preferably, the composition comprises at least three fillers that are different from each other, one of which is chosen from spherical porous silica particles, in particular spherical porous silica microparticles, and the other two are chosen from spherical cellulose particles, powders of an N-acylamino acid bearing a C8-C22 acyl group and polyamide particles, preferably spherical cellulose particles and powders of an N-acylamino acid bearing a C8-C22 acyl group. Even more preferentially, the composition comprises at least three fillers that are different from each other, the first of which is chosen from spherical porous silica particles, in particular spherical porous silica microparticles, the second is chosen from spherical cellulose particles, and the third is chosen from powders of an N-acylamino acid bearing a C8-C22 acyl group.

The composition in accordance with the invention comprises from 10% to 50% by weight and preferably from 15% to 35% by weight of fillers, relative to the total weight of the composition. The composition in accordance with the invention comprises at least 5% by weight of a first filler, preferably 5% to 25% by weight relative to the total weight of the composition, and at least 5% by weight of a second filler, preferably from 5% to 25% by weight relative to the total weight of the composition, the first filler and the second filler being chosen from spherical cellulose particles, powders of an N-acylamino acid bearing a C8-C22 acyl group, polyamide particles and spherical porous silica particles.

When the composition in accordance with the invention comprises at least three fillers that are different from each other, it comprises at least 5% by weight of a first filler, preferably 5% to 25% by weight relative to the total weight of the composition, at least 5% by weight of a second filler, preferably from 5% to 25% by weight relative to the total weight of the composition, and at least 5% by weight of a third filler, preferably 5% to 25% by weight relative to the total weight of the composition, the first, second and third fillers being chosen from spherical cellulose particles, powders of an N-acylamino acid bearing a C8-C22 acyl group, polyamide particles and spherical porous silica particles.

According to a particular embodiment, the composition comprises at least one filler chosen from spherical porous silica particles, in particular spherical porous silica microparticles, and the mass ratio R of silica/fillers other than silica is greater than or equal to 0.75, preferably between 0.75 and 3.

Fatty Phase

The composition in accordance with the invention comprises from 40% to 85% by weight of a fatty phase, relative to the total weight of the composition.

According to a particular embodiment, the composition in accordance with the invention comprises from 45% to 85% by weight of a fatty phase. Preferably, the proportion of the fatty phase ranges from 50% to 85% by weight and even more preferentially from 54% to 77% by weight relative to the total weight of the composition.

This indicated amount does not comprise the content of lipophilic gelling agents such as those described above.

For the purpose of the invention, the fatty phase includes any fatty substance that is liquid at room temperature and atmospheric pressure, generally oils, or that is solid at room temperature and atmospheric pressure, like waxes, or any pasty compound, which are present in said composition.

The fatty substance(s) present in the composition may be chosen by a person skilled in the art on the basis of his general knowledge, so as to give the final composition the desired properties, especially in terms of rheological properties (penetrometry measurement, flow, consistency) or in terms of texture and stability.

Pasty Compound

For the purposes of the present invention, the term "pasty compound" means a lipophilic fatty compound with a reversible solid/liquid change of state, and comprising at a temperature of 23° C. a liquid fraction and a solid fraction.

A pasty compound is, at a temperature of 23° C., in the form of a liquid fraction and a solid fraction. In other words, the starting melting point of the pasty compound is less than 23° C. The liquid fraction of the pasty compound, measured at 23° C., represents from 20% to 97% by weight of the pasty compound. This fraction that is liquid at 23° C. more preferentially represents from 25% to 85% and better still from 30% to 60% by weight of the pasty compound.

The liquid fraction by weight of the pasty compound at 23° C. is equal to the ratio of the heat of fusion consumed at 23° C. to the heat of fusion of the pasty compound.

The heat of fusion consumed at 23° C. is the amount of energy absorbed by the sample to change from the solid state to the state that it has at 23° C., formed from a liquid fraction and a solid fraction.

The heat of fusion of the pasty compound is the enthalpy consumed by the compound in order to pass from the solid state to the liquid state. The pasty compound is said to be in the solid state when all of its mass is in solid form. The pasty compound is said to be in the liquid state when all of its mass is in the liquid form.

The heat of fusion of the pasty compound is equal to the area under the curve of the thermogram obtained using a differential scanning calorimeter (DSC), such as the calorimeter sold under the name MDSC 2920 by the company TA Instruments, with a temperature rise of 5° C. or 10° C. per minute, according to standard ISO 11357-3: 1999. The heat of fusion of the pasty compound is the amount of energy required to make the compound change from the solid state to the liquid state. It is expressed in J/g.

The liquid fraction of the pasty compound measured at 32° C. preferably represents from 40% to 100% by weight of the pasty compound and better still from 50% to 100% by weight of the pasty compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound. The heat of fusion consumed at 32° C. is calculated in the same way as the heat of fusion consumed at 23° C. The pasty compound preferably has a hardness at 20° C. ranging from 0.001 to 0.5 MPa and preferably from 0.002 to 0.4 MPa.

The hardness is measured according to a method of penetration of a probe into a sample of compound and in particular using a texture analyzer (for example the TA-XT2i machine from Rheo) equipped with a stainless-steel cylinder 2 mm in diameter. The hardness measurement is performed at 20° C. at the center of five samples. The cylinder is introduced into each sample, the penetration depth being 0.3 mm. The recorded hardness value is that of the maximum peak.

The pasty compound is chosen from compounds of plant origin. A pasty compound may be obtained via synthesis from starting materials of plant origin.

The pasty compound may be chosen especially from isomerized jojoba oil such as the trans-isomerized partially hydrogenated jojoba oil manufactured or sold by the company Desert Whale under the commercial reference Iso-Jojoba-50®, orange wax, for instance the product sold under the reference Orange Peel Wax by the company Koster Keunen, cupuacu butter (Rain Forest RF3410 from the company Beraca Sabara), murumuru butter (Rain Forest RF3710 from the company Beraca Sabara), shea butter, partially hydrogenated olive oil, for instance the compound sold under the name Beurrolive by the company Soliance, cocoa butter, mango oil, for instance Lipex 203 from the company Aarhuskarlshamn, and mixtures thereof.

Mention may also be made of mixtures of fatty acids comprising from 8 to 30 carbon atoms and of fatty alcohols comprising from 8 to 30 carbon atoms, such as mixtures of lauryl alcohol and methyl laurate, of stearyl alcohol and methyl palmitate or methyl behenate, such as the Purester range sold by the company Strahl & Pitsch, especially the lauryl laurate known under the trade name Purester 24.

Similarly, mention may be made of esters of a fatty acid comprising from 8 to 30 carbon atoms and of polyglycerol comprising from 2 to 10 glyceryl units, such as the polyglyceryl-3 polyricinoleate sold by the company Aarhuskarlshamn under the name Akoline PGPR or alternatively a mixture of three jojoba ester waxes & Helianthus annus seed wax & Acacia decurrens extract and polyglyceryl, such as the product sold under the name Hydracire S or Acticire® by the company Gattefossé.

Mention may also be made of hydrogenated glycerol esters, for instance the product sold under the name Cegesoft HF 52 by the company Cognis (BASF), which is a mixture of hydrogenated rapeseed and palm oils, or the product sold under the name Softisan 100 Cremer by the company Oleo.

Mention may also be made of mixtures of monoester and/or diester of a fatty acid comprising from 8 to 18 carbon atoms and of mono- or polyglycerol, such as glyceryl stearate, for instance the glyceryl stearate sold under the reference Cutina GMS V by the company Cognis or the mixture of glyceryl monostearate and distearate sold by the company Stéarineries Dubois under the name Dub GMS 50/50.

When they are present, the amount of pasty compounds may range, for example, from 0.05% to 85% by weight, better still from 0.1% to 40% by weight and in particular from 0.5% to 10% by weight relative to the total weight of the composition.

Waxes

Besides such a pasty fatty substance, the composition of the invention may also comprise at least one wax.

For the purposes of the present invention, the term "wax" means a lipophilic compound, which is solid at room temperature (25° C.), with a reversible solid/liquid change of state, having a melting point of greater than or equal to 30° C., which may be up to 120° C. In particular, the waxes have a melting point of greater than 30° C. and better still greater than 45° C.

For the purposes of the invention, the melting point corresponds to the temperature of the most endothermic peak observed on thermal analysis (differential scanning calorimetry or DSC) as described in standard ISO 11357-3; 1999. The melting point of the wax may be measured using a differential scanning calorimeter (DSC), for example the calorimeter sold under the name MDSC 2920 by the company TA Instruments.

The measurement protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and it is finally subjected to a second temperature rise ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

For the purposes of the present invention, the term "hard wax" means a wax having, at 20° C., a hardness of greater than 5 MPa, especially ranging from 5 to 30 MPa, preferably greater than 6 MPa and better still ranging from 6 to 25 MPa.

The hardness of the wax is determined by measuring the compressive force, measured at 20° C. using the texturometer sold under the name TA-XT2 by the company Rheo, equipped with a stainless-steel cylinder 2 mm in diameter, traveling at a measuring speed of 0.1 mm/s, and penetrating the wax to a penetration depth of 0.3 mm.

The measuring protocol is as follows: the wax is melted at a temperature equal to the melting point of the wax+10° C. The molten wax is poured into a container 25 mm in diameter and 20 mm deep. The wax is recrystallized at room temperature (25° C.) for 24 hours such that the surface of the wax is flat and smooth, and the wax is then stored for at least 1 hour at 20° C. before measuring the hardness or the tack.

The texturometer spindle is displaced at a speed of 0.1 mm/s, then penetrates the wax to a penetration depth of 0.3 mm. When the spindle has penetrated the wax to a depth of 0.3 mm, the spindle is held still for 1 second (corresponding to the relaxation time) and is then withdrawn at a speed of 0.5 mm/s.

The hardness value is the maximum compression force measured divided by the area of the texturometer cylinder in contact with the wax.

Waxes that may advantageously be used include waxes of plant origin such as beeswax, especially the product sold under the name White Beeswax SP 453P by the company Strahl & Pitsch or Cerabeil LOR by the company Baerlocher, black wheat wax such as the product sold by the company Codif, carnauba wax, candelilla wax, especially the commercial reference Candelilla Wax SP 75 G by the company Strahl & Pitsch, hydrogenated jojoba wax, sumach wax, the waxes obtained by hydrogenation of olive oil esterified with fatty alcohols bearing a C12 to C18 chain, sold by the company Sophim in the Phytowax range (12L44, 14L48, 16L55 and 18L57), rice bran wax, cetyl, stearyl and behenyl alcohols, laurel wax or ouricury wax.

Use may also be made of at least one ester of behenic acid and of glycerol, and in particular a mixture of esters of behenic acid and of glycerol, for instance the glyceryl dibehenate, tribehenin, glyceryl behenate mixture sold by the company Gattefossé under the reference Compritol 888 CG ATO.

When they are present, the waxes may be present in a content ranging from 0.01% to 40% by weight, preferably from 0.05% to 10% by weight and better still from 0.1% to 5% by weight relative to the total weight of the composition.

Oils

The composition according to the invention advantageously comprises at least one oil.

The term "oils" means fatty substances that are liquid at room temperature (25° C.) and atmospheric pressure.

As oils that may be used in the composition of the invention, examples that may be mentioned include:

hydrocarbon-based oils of plant origin, such as squalane, liquid triglycerides of fatty acids comprising from 4 to 30 carbon atoms, for instance heptanoic or octanoic acid triglycerides, or alternatively, for example, jojoba oil, babassu oil, sunflower oil, olive oil, coconut oil, Brazil nut oil, marula oil, corn oil, soybean oil, marrow oil, grapeseed oil, linseed oil, sesame seed oil, hazelnut oil, apricot oil, macadamia nut oil, arara oil, coriander oil, castor oil, avocado oil, caprylic/capric acid triglycerides, for instance those sold by the company Stéarineries Dubois or those sold under the names Miglyol 810, 812 and 818 by the company Dynamit Nobel, and shea butter oil;

synthetic esters and ethers, especially of fatty acids and/or of fatty alcohols, for instance the oils of formulae $R^1COOR^2$ and $R^1OR^2$ in which $R^1CO$ represents a fatty acid residue or $R^1$ represents a fatty alcohol residue containing from 8 to 29 carbon atoms and $R^2$ represents a branched or unbranched hydrocarbon-based chain containing from 3 to 30 carbon atoms, for instance purcellin oil, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alcohol heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

mixtures thereof.

Mention may also be made of the following oils:

esters derived from the reaction of at least one fatty acid containing at least 6 carbon atoms, preferably from 6 to 26 carbon atoms, better still from 6 to 20 carbon atoms and even better still from 6 to 16 carbon atoms, and of at least one alcohol comprising from 1 to 17 carbon atoms and better still from 3 to 15 carbon atoms; mention may in particular be made of isopropyl myristate, such as the products sold under the name Palmester 1510 by the company KLK Oleo, under the name Lexol IPM-NF by the company Inolex Chemical Company or under the name Isopropyl Myristate by the company Cognis (BASF), isopropyl isostearate such as the product sold under the name Radia 7739 by the company Oleon, isopropyl palmitate, 2-ethylhexyl caprate/caprylate (or octyl caprate/caprylate), 2-ethylhexyl palmitate, isostearyl neopentanoate, isononyl isononanoate, hexyl laurate, lactic acid esters of fatty alcohols comprising 12 or 13 carbon atoms, and dicaprylyl carbonate, such as the product which is sold under the name Cetiol CC by the company Cognis, fatty alcohol ethers comprising from 6 to 20 carbon atoms, preferably from 8 to 12 carbon atoms, even more preferentially from 8 to 10 carbon atoms.

These ethers may be obtained from two different fatty alcohols or from two identical fatty alcohols. Preferably, they are obtained from two identical fatty alcohols such as capryl alcohol (also known as 1-octanol or n-octanol). The corresponding ether is then dicaprylyl ether, such as the product sold under the name Cetiol OE by the company Cognis.

glycerol ethers comprising from 6 to 12 carbon atoms, for instance the 2-ethylhexyl ether of glycerol (INCI name: ethylhexyl glycerol) such as Sensiva SC 50 from the company Schulke & Mayr GmbH.

Mention may be made in particular of the mixture of esters of caprylic/capric acids and of C12-C18 fatty alcohols such as coco-caprylate/caprate sold under the name Cetiol LC by the company Cognis or under the name Dub 810 C by the company Stéarineries Dubois;

volatile linear alkanes, advantageously of plant origin, comprising from 7 to 17 carbon atoms, in particular from 9 to 15 carbon atoms and more particularly from 11 to 13 carbon atoms.

As examples of volatile linear alkanes that are suitable for use in the invention, mention may be made of those described in patent application WO 2007/068 371 from the company Cognis.

As examples of volatile linear alkanes that are suitable for use in the invention, mention may be made of n-nonane ($C_9$), n-decane ($C_{10}$), n-undecane ($C_{11}$), n-dodecane ($C_{12}$), n-tridecane ($C_{13}$), n-tetradecane ($C_{14}$), n-pentadecane ($C_{15}$), n-hexadecane ($C_{16}$) and n-heptadecane ($C_{17}$), and mixtures thereof. According to a particularly preferred embodiment, use will be made of a mixture of undecane ($C_{11}$) and of tridecane ($C_{13}$) such as the product sold under the reference Cetiol UT by the company Cognis. Mention may also be made of n-dodecane ($C_{12}$) and n-tetradecane ($C_{14}$) such as those sold by Sasol under the references, respectively, Parafol 12-97 and Parafol 14-97, and also mixtures thereof.

polyesters obtained by condensation of a dimer and/or trimer of a C8-C30 unsaturated fatty acid and of diol, for instance the polyesters of dilinoleic acid and of diol sold by Biosynthis under the name Viscoplast and especially the polymer bearing the INCI name dilinoleic acid/propanediol copolymer;

and mixtures thereof.

Use may also be made of Guerbet alcohols or of Guerbet alcohol derivatives, for instance esters of Guerbet alcohols and of C8-C30 fatty acid. Guerbet alcohols are obtained by converting an aliphatic primary alcohol into a beta-alkylenated alcohol dimer via the following chemical reaction:

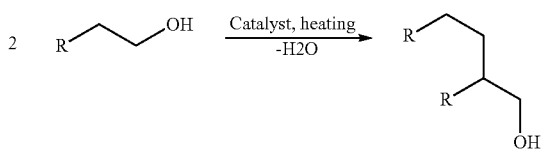

This reaction requires the presence of a base such as alkali metal hydroxides or alkali metal alkoxides, a catalyst such as Raney nickel, and high temperatures.

As Guerbet alcohols or esters of C8-C30 fatty acids and of Guerbet alcohols, mention may be made especially of octyldodecanol and octyldodecanol esters such as octyldodecyl myristate. Mention may be made in particular of octyldodecanol, such as the product sold under the name Eutanol G by the company Cognis (BASF) and the octyldodecyl myristate sold under the name Dub MOD by the company Gattefossé.

The composition according to the invention may have a total oil content ranging from 40% to 85% by weight, preferably from 50% to 85% by weight and better still from 54% to 77% by weight relative to the total weight of the composition.

According to a particular embodiment of the invention, the fatty phase of the composition comprises at least one oil chosen from hydrocarbon-based oils of plant origin, preferably triglycerides, Guerbet alcohols, esters of a C8-C30 fatty acid and of a Guerbet alcohol, and linear C7-C17 alkanes, and mixtures thereof.

According to a particular embodiment, the composition comprises from 40% to 85% by weight of at least one oil chosen from hydrocarbon-based oils of plant origin, preferably triglycerides, Guerbet alcohols, esters of a C8-C30 fatty acid and of a Guerbet alcohol, and linear C7-C17 alkanes, and mixtures thereof.

According to another particular embodiment of the invention, the composition comprises from 15% to 85% by weight of at least one oil chosen from hydrocarbon-based oils of plant origin, preferably triglycerides, Guerbet alcohols and esters of a C8-C30 fatty acid and of a Guerbet alcohol, and optionally from 5% to 25% by weight and preferably from 5% to 10% by weight of at least one oil chosen from linear C7-C17 alkanes.

According to a first specific embodiment of the invention, the anhydrous composition comprises:
  from 3% to 15% by weight of at least one lipophilic gelling agent chosen from fatty acid esters of dextrin, preferably dextrin palmitate;
  from 10% to 50% by weight of fillers including at least 5% by weight of spherical porous silica microparticles and at least 5% by weight of powder of an N-acylamino acid bearing a C8-C22 acyl group, preferably with a mass ratio R of silica/N-acylamino acid bearing a C8-C22 acyl group of greater than or equal to 0.75, preferably between 0.75 and 3; and
  from 40% to 85% by weight of at least one fatty phase comprising at least one oil chosen from hydrocarbon-based oils of plant origin, preferably triglycerides, Guerbet alcohols, esters of a C8-C30 fatty acid and of a Guerbet alcohol, and linear C7-C17 alkanes;
the weight amounts being given relative to the total weight of the composition.

According to a particular embodiment, the anhydrous composition comprises:
  from 3% to 15% by weight of at least one lipophilic gelling agent chosen from fatty acid esters of dextrin, preferably dextrin palmitate;
  from 10% to 50% by weight of fillers including at least 5% by weight of spherical porous silica microparticles and at least 5% by weight of powders of an N-acylamino acid bearing a C8-C22 acyl group, preferably with a mass ratio R of silica/N-acylamino acid bearing a C8-C22 acyl group of greater than or equal to 0.75, and even more preferentially between 0.75 and 3; and
  from 40% to 85% by weight of at least one fatty phase comprising at least one oil chosen from hydrocarbon-based oils of plant origin, preferably triglycerides;
the weight amounts being given relative to the total weight of the composition.

Preferably, the anhydrous composition comprises:
  from 3% to 15% by weight of at least one lipophilic gelling agent chosen from fatty acid esters of dextrin, preferably dextrin palmitate;
  from 10% to 50% by weight of fillers including at least 5% by weight of spherical porous silica microparticles and at least 5% by weight of powders of an N-acylamino acid bearing a C8-C22 acyl group, preferably with a mass ratio R of silica/N-acylamino acid bearing a C8-C22 acyl group of greater than or equal to 0.75, and even more preferentially between 0.75 and 3; and
  from 40% to 85% by weight of at least one fatty phase comprising from 25% to 48% by weight of at least one oil chosen from hydrocarbon-based oils of plant origin, preferably triglycerides;
the weight amounts being given relative to the total weight of the composition.

According to a particular embodiment, the anhydrous composition comprises:
  from 3% to 15% by weight of at least one lipophilic gelling agent chosen from fatty acid esters of dextrin, preferably dextrin palmitate;
  from 10% to 50% by weight of fillers including at least 5% by weight of spherical porous silica microparticles and at least 5% by weight of powders of an N-acylamino acid bearing a C8-C22 acyl group, preferably with a mass ratio R of silica/N-acylamino acid bearing a C8-C22 acyl group of greater than or equal to 0.75, and even more preferentially between 0.75 and 3; and
  from 40% to 85% by weight of at least one fatty phase comprising at least one oil chosen from hydrocarbon-based oils of plant origin, preferably triglycerides and at least one oil chosen from linear C7-C17 alkanes;
the weight amounts being given relative to the total weight of the composition.

Preferably, the anhydrous corn position comprises:
  from 3% to 15% by weight of at least one lipophilic gelling agent chosen from fatty acid esters of dextrin, preferably dextrin palmitate;
  from 10% to 50% by weight of fillers including at least 5% by weight of spherical porous silica microparticles and at least 5% by weight of powders of an N-acylamino acid bearing a C8-C22 acyl group, preferably with a mass ratio R of silica/N-acylamino acid bearing a C8-C22 acyl group of greater than or equal to 0.75, and even more preferentially between 0.75 and 3; and
  from 40% to 85% by weight of at least one fatty phase comprising from 25% to 48% by weight of at least one oil chosen from hydrocarbon-based oils of plant origin, preferably triglycerides and from 5% to 25% by weight and preferably from 5% to 10% by weight of at least one oil chosen from linear C7-C17 alkanes;

the weight amounts being given relative to the total weight of the composition.

According to a second specific embodiment of the invention, the anhydrous composition comprises:
from 3% to 15% by weight of at least one lipophilic gelling agent chosen from fatty acid esters of dextrin, preferably dextrin palmitate;
from 10% to 50% by weight of fillers including at least 5% by weight of spherical porous silica microparticles and at least 5% by weight of spherical cellulose particles, preferably with a mass ratio R of silica/cellulose of greater than or equal to 0.75, and even more preferentially between 0.75 and 3; and
from 40% to 85% by weight of at least one fatty phase comprising at least one oil chosen from hydrocarbon-based oils of plant origin, preferably triglycerides, Guerbet alcohols, esters of a C8-C30 fatty acid and of a Guerbet alcohol, and linear C7-C17 alkanes;

the weight amounts being given relative to the total weight of the composition.

According to a particular embodiment, the anhydrous composition comprises:
from 3% to 15% by weight of at least one lipophilic gelling agent chosen from fatty acid esters of dextrin, preferably dextrin palmitate;
from 10% to 50% by weight of fillers including at least 5% by weight of spherical porous silica microparticles and at least 5% by weight of spherical cellulose particles, preferably with a mass ratio R of silica/cellulose of greater than or equal to 0.75, and even more preferentially between 0.75 and 3; and
from 40% to 85% by weight of at least one fatty phase comprising at least one oil chosen from Guerbet alcohols and esters of a C8-C30 fatty acid and of a Guerbet alcohol;

the weight amounts being given relative to the total weight of the composition.

Preferably, the anhydrous composition comprises:
from 3% to 15% by weight of at least one lipophilic gelling agent chosen from fatty acid esters of dextrin, preferably dextrin palmitate;
from 10% to 50% by weight of fillers including at least 5% by weight of spherical porous silica microparticles and at least 5% by weight of spherical cellulose particles, preferably with a mass ratio R of silica/cellulose of greater than or equal to 0.75, and even more preferentially between 0.75 and 3; and
from 40% to 85% by weight of at least one fatty phase comprising from 25% to 70% by weight and preferably from 25% to 48% by weight of at least one oil chosen from Guerbet alcohols and esters of a C8-C30 fatty acid and of a Guerbet alcohol;

the weight amounts being given relative to the total weight of the composition.

According to a third specific embodiment of the invention, the anhydrous composition comprises:
from 3% to 15% by weight of at least one lipophilic gelling agent chosen from triesters of a C8-C30 fatty acid and of mono- or polyglycerol, such as glyceryl trihydroxystearate;
from 10% to 50% by weight of fillers including at least 5% by weight of spherical porous silica microparticles and at least 5% by weight of spherical cellulose particles, preferably with a mass ratio R of silica/cellulose of greater than or equal to 0.75, and even more preferentially between 0.75 and 3; and
from 40% to 85% by weight of at least one fatty phase comprising at least one oil chosen from hydrocarbon-based oils of plant origin, preferably triglycerides, Guerbet alcohols, esters of a C8-C30 fatty acid and of a Guerbet alcohol, and linear C7-C17 alkanes;

the weight amounts being given relative to the total weight of the composition.

According to a particular embodiment, the anhydrous composition comprises:
from 3% to 15% by weight of at least one lipophilic gelling agent chosen from triesters of a C8-C30 fatty acid and of mono- or polyglycerol, such as glyceryl trihydroxystearate;
from 10% to 50% by weight of fillers including at least 5% by weight of spherical porous silica microparticles and at least 5% by weight of spherical cellulose particles, preferably with a mass ratio R of silica/cellulose of greater than or equal to 0.75, and even more preferentially between 0.75 and 3; and
from 40% to 85% by weight of at least one fatty phase comprising at least one oil chosen from hydrocarbon-based oils of plant origin, preferably triglycerides and at least one oil chosen from linear C7-C17 alkanes;

the weight amounts being given relative to the total weight of the composition.

Preferably, the anhydrous composition comprises:
from 3% to 15% by weight of at least one lipophilic gelling agent chosen from triesters of a C8-C30 fatty acid and of mono- or polyglycerol, such as glyceryl trihydroxystearate;
from 10% to 50% by weight of fillers including at least 5% by weight of spherical porous silica microparticles and at least 5% by weight of spherical cellulose particles, preferably with a mass ratio R of silica/cellulose of greater than or equal to 0.75, and even more preferentially between 0.75 and 3; and
from 40% to 85% by weight of at least one fatty phase comprising from 25% to 48% by weight of at least one oil chosen from hydrocarbon-based oils of plant origin, preferably triglycerides and from 5% to 25% by weight and preferably from 5% to 10% by weight of at least one oil chosen from linear C7-C17 alkanes;

the weight amounts being given relative to the total weight of the composition.

According to a fourth specific embodiment of the invention, the anhydrous composition comprises:
from 3% to 15% by weight of at least one lipophilic gelling agent chosen from fatty acid esters of dextrin, preferably dextrin myristate;
from 10% to 50% by weight of fillers including at least 5% by weight of powders of an N-acylamino acid bearing a C8-C22 acyl group and at least 5% by weight of spherical cellulose particles; and
from 40% to 85% by weight of at least one fatty phase comprising at least one oil chosen from hydrocarbon-based oils of plant origin, preferably triglycerides, Guerbet alcohols, esters of a C8-C30 fatty acid and of a Guerbet alcohol, and linear C7-C17 alkanes;

the weight amounts being given relative to the total weight of the composition.

According to a particular embodiment, the anhydrous composition comprises:
from 3% to 15% by weight of at least one lipophilic gelling agent chosen from fatty acid esters of dextrin, preferably dextrin myristate;

from 10% to 50% by weight of fillers including at least 5% by weight of powders of an N-acylamino acid bearing a C8-C22 acyl group and at least 5% by weight of spherical cellulose particles; and from 40% to 85% by weight of at least one fatty phase comprising at least one oil chosen from Guerbet alcohols and esters of a C8-C30 fatty acid and of a Guerbet alcohol;

the weight amounts being given relative to the total weight of the composition.

Preferably, the anhydrous composition comprises:

from 3% to 15% by weight of at least one lipophilic gelling agent chosen from fatty acid esters of dextrin, preferably dextrin myristate;

from 10% to 50% by weight of fillers including at least 5% by weight of powders of an N-acylamino acid bearing a C8-C22 acyl group and at least 5% by weight of spherical cellulose particles; and from 40% to 85% by weight of at least one fatty phase comprising from 5% to 25% by weight and preferably from 5% to 15% by weight of at least one oil chosen from Guerbet alcohols and esters of a C8-C30 fatty acid and of a Guerbet alcohol;

the weight amounts being given relative to the total weight of the composition.

According to a fifth specific embodiment of the invention, the anhydrous composition comprises:

from 3% to 15% by weight of at least one lipophilic gelling agent chosen from fatty acid esters of dextrin, preferably dextrin myristate;

from 10% to 50% by weight of fillers including at least 5% by weight of spherical porous silica microparticles and at least 5% by weight of spherical cellulose particles; and from 40% to 85% by weight of at least one fatty phase comprising at least one oil chosen from hydrocarbon-based oils of plant origin, preferably triglycerides, Guerbet alcohols, esters of a C8-C30 fatty acid and of a Guerbet alcohol, and linear C7-C17 alkanes;

the weight amounts being given relative to the total weight of the composition.

According to a particular embodiment, the anhydrous composition comprises:

from 3% to 15% by weight of at least one lipophilic gelling agent chosen from fatty acid esters of dextrin, preferably dextrin myristate;

from 10% to 50% by weight of fillers including at least 5% by weight of spherical porous silica microparticles and at least 5% by weight of spherical cellulose particles; and from 40% to 85% by weight of at least one fatty phase comprising at least one oil chosen from Guerbet alcohols and esters of a C8-C30 fatty acid and of a Guerbet alcohol;

the weight amounts being given relative to the total weight of the composition.

Preferably, the anhydrous composition comprises:

from 3% to 15% by weight of at least one lipophilic gelling agent chosen from fatty acid esters of dextrin, preferably dextrin myristate;

from 10% to 50% by weight of fillers including at least 5% by weight of spherical porous silica microparticles and at least 5% by weight of spherical cellulose particles; and from 40% to 85% by weight of at least one fatty phase comprising from 5% to 25% by weight and preferably from 5% to 15% by weight of at least one oil chosen from Guerbet alcohols and esters of a C8-C30 fatty acid and of a Guerbet alcohol;

the weight amounts being given relative to the total weight of the composition.

According to a sixth specific embodiment of the invention, the anhydrous composition comprises:

from 3% to 15% by weight of at least one lipophilic gelling agent chosen from fatty acid esters of dextrin, preferably dextrin myristate;

from 15% to 50% by weight of fillers including at least three fillers that are different from each other, one of which is chosen from mineral fillers and the other two are chosen from organic fillers, preferably at least three fillers that are different from each other, one of which is chosen from spherical porous silica particles, in particular spherical porous silica microparticles, and the other two are chosen from spherical cellulose particles, powders of an N-acylamino acid bearing a C8-C22 acyl group and polyamide particles, preferably spherical cellulose particles and powders of an N-acylamino acid bearing a C8-C22 acyl group; and from 40% to 85% by weight of at least one fatty phase comprising at least one oil chosen from hydrocarbon-based oils of plant origin, preferably triglycerides, Guerbet alcohols, esters of a C8-C30 fatty acid and of a Guerbet alcohol, and linear C7-C17 alkanes;

the weight amounts being given relative to the total weight of the composition.

According to a particular embodiment, the anhydrous composition comprises:

from 3% to 15% by weight of at least one lipophilic gelling agent chosen from fatty acid esters of dextrin, preferably dextrin myristate;

from 15% to 50% by weight of fillers including at least three fillers that are different from each other, one of which is chosen from mineral fillers and the other two are chosen from organic fillers, preferably at least three fillers that are different from each other, one of which is chosen from spherical porous silica particles, in particular spherical porous silica microparticles, and the other two are chosen from spherical cellulose particles, powders of an N-acylamino acid bearing a C8-C22 acyl group and polyamide particles, preferably spherical cellulose particles and powders of an N-acylamino acid bearing a C8-C22 acyl group; and from 40% to 85% by weight of at least one fatty phase comprising at least one oil chosen from Guerbet alcohols and esters of a C8-C30 fatty acid and of a Guerbet alcohol;

the weight amounts being given relative to the total weight of the composition.

Preferably, the anhydrous composition comprises:

from 3% to 15% by weight of at least one lipophilic gelling agent chosen from fatty acid esters of dextrin, preferably dextrin myristate;

from 15% to 50% by weight of fillers including at least three fillers that are different from each other, one of which is chosen from mineral fillers and the other two are chosen from organic fillers, preferably at least three fillers that are different from each other, one of which is chosen from spherical porous silica particles, in particular spherical porous silica microparticles, and the other two are chosen from spherical cellulose particles, powders of an N-acylamino acid bearing a C8-C22 acyl group and polyamide particles, preferably spherical cellulose particles and powders of an N-acylamino acid bearing a C8-C22 acyl group; and from 40% to 85% by weight of at least one fatty phase comprising from 5% to 25% by weight, preferably from 5% to 15% by weight and even more preferentially from 5% to 10% by weight of at least one oil chosen from Guerbet alcohols and esters of a C8-C30 fatty acid and of a Guerbet alcohol;

the weight amounts being given relative to the total weight of the composition.

Even more preferentially, the anhydrous composition comprises:

from 3% to 15% by weight of at least one lipophilic gelling agent chosen from fatty acid esters of dextrin, preferably dextrin myristate;

from 15% to 50% by weight of at least three fillers that are different from each other including at least 5% by weight of a first mineral filler chosen from spherical porous silica particles, in particular spherical porous silica microparticles, at least 5% by weight of at least a second organic filler chosen from spherical cellulose particles, and at least 5% by weight of a third organic filler chosen from powders of an N-acylamino acid bearing a C8-C22 acyl group; and from 40% to 85% by weight of at least one fatty phase comprising from 5% to 25% by weight, preferably from 5% to 15% by weight and even more preferentially from 5% to 10% by weight of at least one oil chosen from Guerbet alcohols and esters of a C8-C30 fatty acid and of a Guerbet alcohol;

the weight amounts being given relative to the total weight of the composition.

The composition according to the invention may also contain one or more polyols comprising from 2 to 8 carbon atoms. The term "polyol" should be understood as meaning any organic molecule comprising at least two free hydroxyl groups. Examples of polyols that may be mentioned include glycerol, glycols, for instance butylene glycol, propylene glycol, isoprene glycol, dipropylene glycol, hexylene glycol, polyethylene glycols and polypropylene glycol and especially dipropylene glycol, 1,2-propanediol and 1,3-propanediol. According to a particular embodiment of the invention, the polyol is chosen from glycerol and 1,3-propanediol. Preferably, the polyol is glycerol.

Examples that may be mentioned include the glycerol sold under the name Glycerine 4810 by the company Oleon or under the name Palmera G995V by the company KLK Oleo or alternatively under the name Refined Glycerine 99.5% PH. EURO by the company Cargill.

Mention may also be made of the 1,3-propanediol sold under the name Zemea Propanediol by the company Dupont Tate and Lyle Bio Products.

Mention may also be made of the butylene glycol sold under the name 1,3-Butylene Glycol by the company Alzo or alternatively Daicel.

Mention may also be made of the propylene glycol sold under the name Radianol 4710 by the company Oleon.

The amount of polyols may range, for example, from 0% to 20% by weight, preferably from 3% to 17% by weight, better still from 4% to 15% by weight and even better still from 5% to 10% by weight, relative to the total weight of the composition.

The composition in accordance with the invention may also comprise one or more primary alcohols, i.e. an alcohol comprising from 1 to 6 carbon atoms, such as ethanol, propanol, isopropanol, butanol, pentanol or hexanol, and in particular ethanol and isopropanol. It is preferably ethanol.

The addition of such an alcohol may especially be suitable when the composition according to the invention is used as a product for the body, the face or the hair.

The amount of primary alcohols may range, for example, from 0% to 35% by weight, preferably from 1% to 15% by weight and even more preferentially from 5% to 10% by weight, relative to the total weight of the composition.

The composition of the invention may contain one or more of the adjuvants that are common in the cosmetic and dermatological fields, such as surfactants; moisturizers; hydrophilic or lipophilic active agents; free-radical scavengers; antioxidants; preserving agents; fragrances; film-forming agents; nacres; pigments; dyes; and mixtures thereof.

The composition in accordance with the invention may comprise one or more active agents.

Nonlimiting examples of active agents that may be mentioned include ascorbic acid and derivatives thereof such as 5,6-di-O-dimethylsilyl ascorbate (sold especially by the company Exsymol under the reference PRO-AA), the potassium salt of dl-alpha-tocopheryl-2l-ascorbyl phosphate (sold especially by the company Senju Pharmaceutical under the reference Sepivital EPC), magnesium ascorbyl phosphate, sodium ascorbyl phosphate (sold especially by the company Roche under the reference Stay-C 50); phloroglucinol; enzymes; and mixtures thereof. According to a preferred embodiment of the invention, use is made, among oxidation-sensitive hydrophilic active agents, of ascorbic acid. The ascorbic acid may be of any nature. Thus, it may be of natural origin in powder form or in the form of orange juice, preferably orange juice concentrate. It may also be of synthetic origin, preferably in powder form.

As other active agents that may be used in the composition of the invention, examples that may be mentioned include moisturizers, such as protein hydrolyzates; natural extracts; anti-inflammatories; oligomeric proanthocyanidins; vitamins such as vitamin A (retinol), vitamin E (tocopherol) and other antioxidants such as extract of rosemary, vitamin B5 (panthenol), vitamin B3 (niacinamide), derivatives of these vitamins (especially esters) and mixtures thereof; urea; caffeine; adenosine; depigmenting agents such as kojic acid, hydroquinone and caffeic acid; salicylic acid and derivatives thereof; alpha-hydroxy acids, such as lactic acid and glycolic acid and derivatives thereof; retinoids, such as carotenoids and vitamin A derivatives; hydrocortisone; melatonin; extracts of algae, of fungi, of plants, of yeasts, of bacteria; steroids; antibacterial active agents; matt-effect agents, for instance fibers; tensioning agents, waxes; UV-screening agents; essential oils; ceramides; and mixtures thereof.

The amounts of these various adjuvants and/or active agents are those conventionally used in the fields under consideration. In particular, these amounts vary according to the desired aim and may range, for example, from 0.01% to 20% and preferably from 0.1% to 10% by weight relative to the total weight of the composition.

Needless to say, a person skilled in the art will take care to select the optional adjuvant(s) and/or active agent(s) added to the composition according to the invention such that the advantageous properties intrinsically associated with the composition in accordance with the invention are not, or are not substantially, adversely affected by the envisioned addition.

The composition according to the invention may be used for any topical application; in particular, it may constitute a cosmetic or dermatological composition, preferably a cosmetic composition, and in particular in the cosmetic field with immediate perceived efficacy. It may in particular be used for caring for and/or removing makeup from the skin, the lips and/or the eyes, and also as a haircare composition. It may also be used as a deodorant or as an antisun product, and also for cleansing the skin.

The composition in accordance with the invention may especially be used as a product for cosmetic use for caring for the skin with regard to antiaging care, greasy skin, antisun protection, antiperspirants and deodorants, hair and/or scalp products, and also styling products, fragrancing products and makeup products.

A subject of the invention is also the cosmetic use of a composition as defined above, for caring for, removing makeup from and/or cleansing the skin, the lips and/or the eyes, and/or for haircare.

A subject of the present invention is also a cosmetic process for removing makeup from and/or caring for the skin, the lips and/or the eyes, in which a composition as defined above is applied to the skin, the lips and/or the eyes.

A subject of the present invention is also a cosmetic haircare process, in which a composition as defined above is applied to the hair.

A subject of the present invention is also a cosmetic treatment process for hiding skin color imperfections and/or skin relief imperfections.

According to a preferred embodiment of the invention, the composition is a composition for caring for bodily and/or facial skin, preferably facial skin.

A subject of the present invention is also an aqueous composition in the form of a dispersion of at least one anhydrous composition as defined previously in an aqueous phase.

The composition in accordance with the invention may be obtained in the usual manner by those skilled in the art.

According to a particular embodiment, the composition in accordance with the invention is obtained according to the following process:
1) wetting the gelling agent with the fatty phase without heating;
2) heating until a temperature of 70° C. to 80° C. is obtained, depending on the case;
3) gelling at 70° C. to 80° C., depending on the case, for 15 minutes with an emulsifying machine, the maximum speed being adapted to the volume manufactured;
4) cooling until a temperature of 35° C. is obtained;
5) adding the fillers at 35° C., with an emulsifying machine. Dispersing until the lumps have disappeared and a homogeneous fluid of smooth, matt macroscopic appearance is obtained;
6) emptying the tank.

According to another particular embodiment, the composition in accordance with the invention is obtained according to the following process:
1) heating the fatty phase until a temperature of 70° C. to 80° C. is obtained, depending on the case;
2) adding the gelling agent and gelling at 70° C. to 80° C., depending on the case, for 15 minutes with an emulsifying machine, the maximum speed being adapted to the volume manufactured;
3) cooling until a temperature of 35° C. is obtained;
4) adding the fillers at 35° C. Dispersing until the lumps have disappeared and a homogeneous fluid of smooth, matt macroscopic appearance is obtained;
5) emptying the tank.

The examples that follow will allow the invention to be understood more clearly, without, however, being limiting in nature. The raw materials are referred to by their chemical or INCI name. The amounts indicated are weight percentages of raw materials, unless otherwise mentioned.

EXAMPLES

Compositions 1 to 12 below were prepared.

| Composition | 1 | 2 | 3 | 4 | 5 |
|---|---|---|---|---|---|
| Silica (Silica Beads SB-300 from the company Miyoshi Kasei) | 25 | 15 | 17.5 | 25 | — |
| Lauroyl lysine (Amihope LL from Ajinomoto) | 10 | 20 | — | — | 7 |
| Cellulose (Cellulobeads USF from Daito Kasei) | — | — | 12.5 | 10 | 8 |
| Dextrin palmitate (Rheopearl TL2-OR from Chiba Flour Milling) | 10 | 10 | 8.5 | — | — |
| Dextrin myristate (Rheopearl MKL2 from Chiba Flour Milling) | — | — | — | — | 9.5 |
| Trihydroxystearin (Thixcin R from Elementis) | — | — | — | 5 | — |
| Caprylic/capric triglyceride (Myritol 318 from Cognis (BASF)) | 26.95 | 30.95 | — | 46 | — |
| Octyldodecyl myristate (MOD from Gattefossé) | — | — | 37 | — | — |
| Isopropyl myristate (Isopropyl myristate from Cognis) | — | — | — | — | 30.1 |
| Octyldodecanol (Eutanol G from Cognis) | — | — | — | — | 10 |
| *Prunus armeniaca* kernel oil (Lipovol P from Lipo Chemicals) | 10 | 10 | 10 | — | 10 |
| Isopropyl palmitate (Isopropyl palmitate from Cognis) | 13 | 14 | 14.45 | — | — |
| Cocoyl caprylate/caprate (Cetiol LC from Cognis) | — | — | — | — | 10 |
| Dicaprylyl Ether (Cetiol OE from Cognis) | — | — | — | — | 10 |
| Undecane (and) tridecane (Cetiol UT from Cognis) | 5 | — | — | 9 | — |
| Candelilla cera (Candelilla Wax SP 75 G from Strahl & Pitsch) | — | — | — | 5 | — |
| Alcohol | — | — | — | — | 5 |
| Fragrance | — | — | — | — | 0.3 |
| Antioxidant | 0.05 | 0.05 | 0.05 | — | 0.1 |

| Composition | 6 | 7 | 8 | 9 | 10 |
|---|---|---|---|---|---|
| Silica (Silica Beads SB-300 from the company Miyoshi Kasei) | 5 | 5 | 5 | 5 | — |
| Lauroyl lysine (Amihope LL from Ajinomoto) | — | 5 | 5 | 5 | 7 |
| Cellulose (Cellulobeads USF from Daito Kasei) | 10 | 5 | 5 | 5 | 8 |

-continued

| | | | | | |
|---|---|---|---|---|---|
| Dextrin palmitate (Rheopearl TL2-OR from Chiba Flour Milling) | — | — | — | — | — |
| Dextrin myristate (Rheopearl MKL2 from Chiba Flour Milling) | 8.5 | 8.5 | 8.5 | 8.5 | 8.5 |
| Isopropyl myristate (Isopropyl myristate from Cognis) | 52 | 24.1 | 19.1 | 19.1 | 24.1 |
| Octyldodecanol (Eutanol G from Cognis) | 14.1 | 10 | 10 | 10 | 10 |
| Prunus armeniaca kernel oil (Lipovol P from Lipo Chemicals) | 10 | 10 | 10 | 5 | 10 |
| Hydrogenated cocoyl glycerides (Softisan 100 from Cremer Oleo) | — | 1 | 5 | 5 | 1 |
| Cocoyl caprylate/caprate (Cetiol LC from Cognis) | — | 10 | 10 | 10 | 10 |
| Glyceryl dibehenate (and) tribehenin (and) glyceryl behenate (Compritol 888 CG ATO from Gattefossé) | — | 2 | 3 | 3 | 2 |
| Dicaprylyl Ether (Cetiol OE from Cognis) | — | 10 | 10 | 10 | 10 |
| Glycerol | — | — | — | 5 | — |
| Glyceryl stearate (Dub GMS 50/50 from Stéarineries Dubois) | — | 4 | 4 | 4 | 4 |
| Alcohol | — | 5 | 5 | 5 | 5 |
| Fragrance | 0.3 | 0.3 | 0.3 | 0.3 | 0.3 |
| Antioxidant | 0.1 | 0.1 | 0.1 | 0.1 | 0.1 |

| Composition | 11 | 12 |
|---|---|---|
| Silica (Silica Beads SB-300 from the company Miyoshi Kasei) | 15 | 15 |
| Lauroyl lysine (Amihope LL from Ajinomoto) | 20 | 20 |
| Dye(s) | qs | qs |
| Dextrin palmitate (Rheopearl TL2-OR from Chiba Flour Milling) | 10 | 10 |
| Caprylic/capric triglyceride (Myritol 318 from Cognis) | 27.7 | 26.7 |
| Prunus armeniaca kernel oil (Lipovol P from Lipo Chemicals) | 7 | 7 |
| Isopropyl palmitate (Isopropyl palmitate from Cognis) | 14 | 14 |
| Cera alba (Cerabeil LOR from Baerlocher) | — | 1 |
| Glycerol | 3 | 3 |
| Alcohol | 3 | 3 |
| Antioxidant | 0.3 | 0.3 |

Preparation Process

The fatty phase is homogenized. After introducing the gelling agent, gelling phase once the desired temperature has been reached (70° C. to 80° C., depending on the case).

Cooling phase, followed by adding any other ingredient of the formulation, where appropriate, and then the fillers (temperature ranging from 50° C. to 32° C.).

Characterization of the Optical Properties

The optical properties of compositions 1 to 10 were characterized by means of the Haze measurement (veil effect) with a commercial Hazemeter machine.

The measurements were taken according to the following protocol: on a transparent plastic film (Byk), a coat with a wet thickness of 25.4 μm of the composition whose haze it is desired to evaluate is spread out, using an automatic spreader. The coat is left to dry for 1 hour at room temperature, and measurement of the haze index is then taken using a Byk Gardner brand Haze-gard.

The values obtained for compositions 1 to 10 are the following:

| | Composition | | | | | |
|---|---|---|---|---|---|---|
| | 1 | 2 | 3 | 4 | 5 | 6 |
| Measured Haze | 86.7 | 90 | 87 | >90 | 60.2 | 61.5 |

| | Composition | | | | | |
|---|---|---|---|---|---|---|
| | 7 | 8 | 9 | 10 | 11 | 12 |
| Measured Haze | 61.9 | 67.8 | 67.4 | 69.8 | 97.9 | 98.7 |

As a guide, it is considered that, between 20 and 60, a weak soft-focus effect was obtained, between 60 and 80, a good soft-focus effect was obtained, and, at and above 90, a very good soft-focus effect was obtained.

These measurements thus show that the compositions in accordance with the invention make it possible to obtain a large soft-focus effect.

Sensory Evaluation:

The sensory properties of compositions 1 to 12 were evaluated after applying them to the skin. The results are summarized in the following table:

| Composition | Sensory properties |
|---|---|
| 1 | rapid penetration, not tacky, not glossy, no film or white film, velvety skin finish |
| 2 | rapid penetration, not glossy, not tacky, no film, very soft skin finish and powdery sensation |
| 3 | rapid penetration, not tacky, not glossy, powdery skin finish |
| 4 | not evaluated |
| 5 | relatively slow penetration, soft skin finish, very slightly tacky, film-forming effect with an oily feel |
| 6 | powdery and soft, dry skin finish, not tacky |
| 7 | slow penetration, greasy texture with transformation to a soft feel, very slightly film-forming and tacky |
| 8 | relatively rapid penetration, not glossy, not tacky, not film-forming, powdery skin finish |
| 9 | relatively slow penetration with moderate glidance, slightly film-forming and tacky, powdery skin finish |
| 10 | rapid penetration, slightly glossy, not tacky, relatively film-forming, powdery skin finish |
| 11 | rapid penetration, not glossy, not tacky, very soft skin finish and powdery sensation |
| 12 | rapid penetration, not glossy, not tacky, very soft skin finish and powdery sensation |

The sensory properties of compositions 1 to 12 according to the invention are good, and especially in terms of soft skin finish and absence of tack.

Stability

The stability of compositions 1 to 12 was evaluated over a period of 2 months at room temperature (25° C.).

All the compositions are stable after 2 months of storage at 25° C.

The invention claimed is:

1. An anhydrous composition comprising: based on a total weight of the composition,
   from 3% to 15% by weight of at least one lipophilic gelling agent;
   from 10% to 50% by weight of fillers including at least 5% by weight of a first filler and at least 5% by weight of a second filler different from the first; and
   from 40% to 85% by weight of at least one fatty phase;
   wherein the first filler and the second filler are selected from the group consisting of spherical cellulose particles, powders of an N-acylamino acid comprising a C8-C22 acyl group, polyamide particles, and spherical porous silica particles.

2. The composition of claim 1, wherein the at least one lipophilic gelling agent is selected from the group consisting of a fatty acid ester of dextrin and a fatty acid of a triester of a C8-C30 fatty acid and of mono- or polyglycerol.

3. The composition of claim 2, wherein the at least one lipophilic gelling agent is a fatty acid ester of dextrin, wherein the fatty acid ester of dextrin is a mono- or polyester of dextrin and of at least one fatty acid of formula (C):

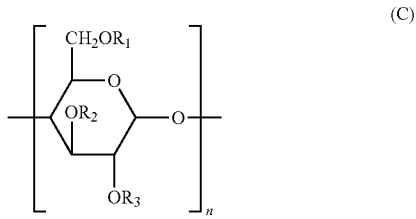

(C)

where:
n is an integer ranging from 3 to 150;
$R_1$, $R_2$ and $R_3$ each independently represent a hydrogen atom or an acyl group (R—CO—) in which R is a linear or branched, saturated or unsaturated hydrocarbon-based group containing from 6 to 50 carbon atoms, with the proviso that at least one of $R_1$, $R_2$ and $R_3$ is not a hydrogen atom.

4. The composition of claim 3, wherein the fatty acid ester of dextrin is a compound of formula (C) where:
n ranges from 25 to 35;
R—CO— is selected from the group consisting of caprylyl, caproyl, lauroyl, myristyl, palmityl, stearyl, eicosanyl, docosanoyl, isovaleryl, 2-ethylbutyryl, ethylmethylacetyl, isoheptanyl, 2-ethylhexanyl, isononanyl, isodecanyl, isotridecanyl, isomyristyl, isopalmityl, isostearyl, isohexanyl, decenyl, dodecenyl, tetradecenyl, myristyl, hexadecenoyl, palmitolyl, oleyl, elaidyl, eicosenyl, sorbyl, linoleyl, linolenyl, punicyl, arachidonyl, stearolyl, and a mixture thereof.

5. The composition of claim 2, wherein the at least one lipophilic gelling agent is a fatty acid of the triester of a C8-C30 fatty acid and of mono- or polyglycerol, wherein the fatty acid of the triester of a C8-C30 fatty acid and of mono- or polyglycerol is a linear or branched, saturated or unsaturated acid comprising from 10 to 24 carbon atoms and unsubstituted or substituted with one or more hydroxyl groups.

6. The composition of claim 5, in which the triester of a C8-C30 fatty acid and of mono- or polyglycerol is a triester of a C8-C30 fatty acid and of monoglycerol.

7. The composition of claim 1, wherein the first filler and the second filler are selected from the group consisting of spherical cellulose particles, powders of an N-acylamino acid comprising a C8-C22 acyl group, and spherical porous silica particles.

8. The composition of claim 1, wherein the first or the second filler is a powder of lauroyl lysine.

9. The composition of claim 1, wherein the first or the second filler is spherical porous silica microparticles.

10. The composition of claim 1, comprising at least two different fillers selected from the group consisting of spherical cellulose particles and powders of an N-acylamino acid comprising a C8-C22 acyl group.

11. The composition of claim 1, comprising at least two different fillers, one of which is spherical cellulose particles, powders of an N-acylamino acid comprising a C8-C22 acyl group, or polyamide particles, and the other is spherical porous silica particles.

12. The composition of claim 1, comprising at least two different fillers, one of which is spherical cellulose particles and the other is spherical porous silica particles.

13. The composition of claim 1, comprising at least two different fillers, one of which is powders of an N-acylamino acid comprising a C8-C22 acyl group, and the other is spherical porous silica particles.

14. The composition of claim 1, comprising at least three fillers that are different from each other, one of which is spherical porous silica particles, and the other two are selected from the group consisting of spherical cellulose particles, powders of an N-acylamino acid comprising a C8-C22 acyl group, and polyamide particles.

15. The composition of claim 1, comprising at least one filler which is spherical porous silica particles, and a mass ratio R of silica/fillers other than silica is greater than or equal to 0.75.

16. The composition of claim 1, wherein the at least one fatty phase comprises at least one oil.

17. The composition of claim 16, comprising from 15% to 85% by weight of at least one oil selected from the group consisting of a hydrocarbon-based oil of plant origin, a Guerbet alcohol, and an ester of a C8-C30 fatty acid and of a Guerbet alcohol.

18. The composition of claim 1, comprising:
from 3% to 15% by weight of the at least one lipophilic gelling agent, which is a fatty acid ester of dextrin;
from 10% to 50% by weight of fillers including at least 5% by weight of spherical porous silica microparticles and at least 5% by weight of powders of an N-acylamino acid comprising a C8-C22 acyl group, a mass ratio R of silica/N-acylamino acid comprising a C8-C22 acyl group being greater than or equal to 0.75; and
from 40% to 85% by weight of the at least one fatty phase comprising from 25% to 48% by weight of at least one hydrocarbon-based oil of plant origin.

19. The composition of claim 1, comprising:
from 3% to 15% by weight of the at least one lipophilic gelling agent, which is a fatty acid ester of dextrin;
from 10% to 50% by weight of fillers including at least 5% by weight of spherical porous silica microparticles and at least 5% by weight of powders of an N-acylamino acid comprising a C8-C22 acyl group, a mass ratio R of silica/N-acylamino acid comprising a C8-C22 acyl group being greater than or equal to 0.75; and
from 40% to 85% by weight of the at least one fatty phase comprising from 25% to 48% by weight of at least one hydrocarbon-based oil of plant origin and from 5% to 25% by weight of at least one linear C7-C17 alkane.

20. The composition of claim 1, comprising:
from 3% to 15% by weight of the at least one lipophilic gelling agent, which is a fatty acid ester of dextrin;
from 10% to 50% by weight of fillers including at least 5% by weight of spherical porous silica microparticles and at least 5% by weight of spherical cellulose particles, a mass ratio R of silica/cellulose being greater than or equal to 0.75; and
from 40% to 85% by weight of the at least one fatty phase comprising from 25% to 70% by weight of at least one oil selected from the group consisting of a Guerbet alcohol and an ester of a C8-C30 fatty acid and of a Guerbet alcohol.

21. The composition of claim 1, comprising:
from 3% to 15% by weight of the at least one lipophilic gelling agent, which is a triester of a C8-C30 fatty acid and of mono- or polyglycerol;
from 10% to 50% by weight of fillers including at least 5% by weight of spherical porous silica microparticles and at least 5% by weight of spherical cellulose particles, a mass ratio R of silica/cellulose being greater than or equal to 0.75; and from 40% to 85% by weight of the at least one fatty phase comprising from 25% to 48% by weight of at least one hydrocarbon-based oil of plant origin and from 5% to 25% by weight of at least one linear C7-C17 alkane.

22. A cosmetic process for treating a keratin material, the process comprising: applying the composition of claim 1 to the keratin material.

23. An aqueous dispersion composition, comprising at least one composition of claim 1 in an aqueous phase.

24. The composition of claim 1, An anhydrous composition comprising: based on a total weight of the composition, from 3% to 15% by weight of at least one lipophilic gelling agent, wherein the at least one lipophilic gelling agent is a fatty acid ester of dextrin, wherein the fatty acid ester of dextrin is a mono- or polyester of dextrin and of at least one fatty acid of formula (C):

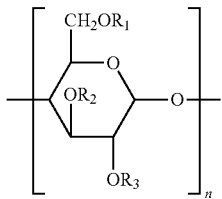

(C)

where:
n is an integer ranging from 3 to 150;
$R_1$, $R_2$ and $R_3$ each independently represent a hydrogen atom or an acyl group (R—CO—) in which R is a linear or branched, saturated or unsaturated hydrocarbon-based group containing from 6 to 50 carbon atoms, with the proviso that at least one of $R_1$, $R_2$ and $R_3$ is not a hydrogen atom;
from 10% to 50% by weight of fillers including at least 5% by weight of a first filler and at least 5% by weight of a second filler different from the first; and
from 40% to 85% by weight of at least one fatty phase; wherein the first filler is spherical porous silica microparticles and the second filler is selected from the group consisting of spherical cellulose particles, powders of an N-acylamino acid comprising a C8-C22 acyl group, and polyamide particles, and
wherein the composition has a haze value of 60 or greater.

25. The composition of claim 1, wherein the composition has a haze value of from 60.2 to 98.7.

26. The composition of claim 1, wherein the composition lacks pigments, dyes and nacres.

27. The composition of claim 18, wherein the composition has a haze value of 60 or greater.

28. The composition of claim 19, wherein the composition has a haze value of 60 or greater.

29. The composition of claim 20, wherein the composition has a haze value of 60 or greater.

30. The composition of claim 21, wherein the composition has a haze value of 60 or greater.

* * * * *

UNITED STATES PATENT AND TRADEMARK OFFICE
CERTIFICATE OF CORRECTION

| | |
|---|---|
| PATENT NO. | : 11,253,464 B2 |
| APPLICATION NO. | : 15/322675 |
| DATED | : February 22, 2022 |
| INVENTOR(S) | : Page et al. |

It is certified that error appears in the above-identified patent and that said Letters Patent is hereby corrected as shown below:

In the Claims

In Column 31, Claim 24, Line 10, delete "The composition of claim 1,".

Signed and Sealed this
Eighth Day of November, 2022

Katherine Kelly Vidal
*Director of the United States Patent and Trademark Office*